(12) United States Patent
Viola et al.

(10) Patent No.: US 11,617,688 B2
(45) Date of Patent: Apr. 4, 2023

(54) DEVICE AND METHOD FOR FOLDING WEB MATERIAL IN A PLANT AND PROCESS FOR PRODUCING LAYERED COMPOSITE ARTICLES

(71) Applicant: M.D. VIOLA MACCHINE S.R.L., Valle Salimbene (IT)

(72) Inventors: Marco Viola, Valle Salimbene (IT); Andrea Viola, Valle Salimbene (IT); Davide Viola, Valle Salimbene (IT)

(73) Assignee: M.D. VIOLA MACCHINE S.R.L., Valle Salimbene (IT)

( * ) Notice: Subject to any disclaimer, the term of this patent is extended or adjusted under 35 U.S.C. 154(b) by 183 days.

(21) Appl. No.: 17/293,068

(22) PCT Filed: Nov. 28, 2019

(86) PCT No.: PCT/IB2019/060283
§ 371 (c)(1),
(2) Date: May 12, 2021

(87) PCT Pub. No.: WO2020/121103
PCT Pub. Date: Jun. 18, 2020

(65) Prior Publication Data
US 2021/0275361 A1    Sep. 9, 2021

(30) Foreign Application Priority Data

Dec. 12, 2018  (IT) .................. 102018000011041

(51) Int. Cl.
*A61F 13/15*    (2006.01)
*B65H 45/22*    (2006.01)

(52) U.S. Cl.
CPC ....... *A61F 13/15747* (2013.01); *B65H 45/22* (2013.01); *B65H 2404/25* (2013.01); *B65H 2404/2693* (2013.01); *B65H 2801/57* (2013.01)

(58) Field of Classification Search
None
See application file for complete search history.

(56) References Cited

U.S. PATENT DOCUMENTS 3,398,656 A      8/1968  Cloud
2016/0228303 A1  8/2016  Wada

OTHER PUBLICATIONS

Feb. 27, 2020 Search Report issued in International Patent Application No. PCT/IB2019/060283.
Feb. 27, 2020 Written Opinion issued in International Patent Application No. PCT/IB2019/060283.

*Primary Examiner* — Barbara J Musser
(74) *Attorney, Agent, or Firm* — Oliff PLC

(57) ABSTRACT

A device for folding web material in a plant for producing layered composite articles includes: a first guide defining a feeding plane for feeding a web material; a second guide positioned downstream of the first guide and defining a receiving plane for receiving the web material, wherein the receiving plane is substantially orthogonal to the feeding plane. A folder is arranged between the first guide and the second guide and includes an elongated edge having a first end close to the first guide and a second end close to the second guide. The elongated edge is extended from the first guide towards the second guide in the receiving plane and away from the feeding plane, in order to progressively move an intermediate portion of the web material away from the feeding plane and fold in two the web material as it travels from the first guide towards the second guide.

14 Claims, 9 Drawing Sheets

FIG.11

Feeding a web material along an advancing direction and from a first guide defining a feeding plane for feeding the web material towards a second guide defining a receiving plane for receiving the web material, in which the second guide is positioned downstream of the first guide with respect to the advancement direction, in which the receiving plane is substantially orthogonal to the feeding plane.

↓

Placing a middle line portion of the web material in contact with an elongated edge of a folder arranged between the first guide and the second guide.

↓

Moving the middle line portion of the web material along the receiving plane and away from the feeding plane and from opposite longitudinal edges of said web material, by sliding the middle line portion on the elongated edge as it travels from the first guide towards the second guide, so as to bend in half said web material up to moving the opposite longitudinal edges close to each other.

↓ ↓

Orienting the folder around an adjustment axis arranged near the second guide and lying in the receiving plane, in order to vary a position of a first end of said elongated edge with respect to the first guide so as to adjust a mutual alignment of the opposite longitudinal edges that are fit next to each other after folding.

Moving the middle line portion also comprises: accompanying and/or driving the middle line portion of the web material from the first guide towards the second by means of a motorized conveyor arranged along the elongated edge.

DEVICE AND METHOD FOR FOLDING WEB MATERIAL IN A PLANT AND PROCESS FOR PRODUCING LAYERED COMPOSITE ARTICLES

FIELD OF THE INVENTION

The object of the present invention is a device and a method for folding web material in a plant and process for producing layered composite articles. In particular, the present invention is situated in the field of production of layered composite articles formed by sheets of fabric and/or non-woven fabric (TNT) and possible further elements such to give the articles the desired properties (such as: impermeability, absorption, breathability, elasticity, etc.). Such articles can for example be articles of clothing. Preferably but not exclusively, the present invention is situated in the field of production lines for producing sanitary articles, in particular pull-up baby diapers and adult diapers, whose packaging is executed starting from different semi-finished products, including webs of material wound in reels, such as, for example, polyethylene, non-woven fabric, cellulose wadding (tissue).

STATE OF THE ART

In the production lines of sanitary items, the web materials are unwound from reels in order to be subsequently fed to processing stations which provide for combining them with each other and possibly with other materials, in order to form a semi-finished product constituted by a layered composite web.

In the production of pull-up diapers, for example, it is known to package a semi-finished product constituted by a layered composite web which is subsequently shaped, in order to obtain a series of diapers that are open and joined together. The layered composite web is the longitudinally folded in two and welded, so as to obtain a series of closed diapers that are joined together. The abovementioned composite web is then cut to obtain the single diapers. Such operations are carried out while the layered composite web continuously advances long a feeding path in a plant for producing the abovementioned diapers.

It is known the execute the longitudinal folding of the layered composite web by means of a folder defined by a flattened body which is vertically arranged between a first guide, defining a horizontal feeding plane for feeding the layered composite web, and a second guide, defining a vertical receiving plane for receiving the layered composite web, in which the second guide is positioned downstream of the first guide with respect to a feed direction of said layered composite web.

The layered composite web is then advanced from the first guide towards the second guide and is kept under traction at opposite longitudinal edges thereof and longitudinally driven. While the layered composite web advances, a longitudinal middle line portion (corresponding to the crotch of the pull-up diapers) of the layered composite web slides against a lower edge of the flattened body and is progressively moved downward by the abovementioned fixed lower edge while the opposite longitudinal edges (corresponding to the waist of the pull-up diapers) are maintained at a greater height and are brought close to each other until they touch. In this manner, the layered composite web is folded halfway along the longitudinal middle line portion thereof. A folding unit of the above-illustrated type is for example schematically described in EP1410778.

Also the document US 2016/228303 (published also as EP3037078) illustrates a folding unit which folds a sheet in two while this advances. The folding unit comprises a belt wound on pulleys and moved along a closed path by a motor in order to operate as a friction reduction mechanism. The document U.S. Pat. No. 3,398,656 illustrates an apparatus for producing packages from a web material. The apparatus is provided with a device for folding the web material.

OBJECTS OF THE INVENTION

The Applicant has observed that often after the folding, due to the deformations and/or sliding of the layered composite web which is subjected to stresses during transport, the opposite longitudinal edges are misaligned with respect to each other. For example, if the web material slides substantially horizontally, one of the two edges is placed higher than the other.

In particular, the Applicant has observed that in the case of production of pull-up diapers, zones of the opposite longitudinal edges which must be mutually joined (corresponding to the sides of each diaper), e.g. via welding, are not correctly aligned and do not mate as they should.

The Applicant has therefore observed that such misalignment can lead to executing defective junctions in the welding station(s) placed downstream.

The Applicant has also observed that such defects can lead to making defective layered composite articles (e.g. of pull-up diapers which are broken at the junctions/welds while they are worn) and/or which even produce only an unpleasant aesthetic impression since, for example, they are asymmetric.

In such context, the Applicant therefore set the object of proposing a device and a method for folding web material in a plant for producing layered composite articles, which allow first of all maintaining a desired and predefined relative position of the opposite longitudinal edges of the web material after the folding, in particular ensuring the mutual alignment of said longitudinal edges, and hence improving the quality of the layered composite articles obtained therefrom.

The Applicant has also set the objective of proposing a device and a method for folding web material which allow improving the quality of the junctions, preferably welds, executed on said web material after the folding.

The Applicant has also set the objective of proposing a device and a method for folding web material which allow obtaining the abovementioned result in a simple and effective manner.

The Applicant has also set the objective of proposing a device and a method for folding web material which can be easily adapted to different sizes/characteristics of the produced layered articles.

The Applicant has also set the objective of proposing a device for folding web material which, in addition to the above-indicated objectives, is also structurally simple, inexpensive and easy to manage and maintain.

SUMMARY OF THE INVENTION

The Applicant has found that such further objectives and objects can be obtained by means of a device and a method in accordance with the present invention, of the type claimed in the enclosed claims and/or described in the following aspects.

In particular, the Applicant has found that such further objectives and objects can be obtained by orienting the flattened body around an adjustment axis lying in a vertical plane, in a manner so as to move one end of said flattened body close to the first guide with respect to said first guide.

In particular, in accordance with a first aspect, the present invention relates to a device for folding web material in a plant for producing layered composite articles, preferably pull-up diapers, comprising:
a first guide defining a feeding plane for feeding a web material;
a second guide defining a receiving plane for receiving the web material, in which the second guide is positioned downstream of the first guide with respect to a feed direction of said web material, in which the receiving plane is substantially orthogonal to the feeding plane;
a folder arranged between the first guide and the second guide and comprising an elongated edge extended between the first guide and the second guide and having a first end close to the first guide and a second end close to the second guide;
in which the elongated edge is extended from the first guide towards the second guide in the receiving plane and away from the feeding plane, in order to progressively move an intermediate portion of the web material away from the feeding plane and fold in two said web material as it travels from the first guide towards the second guide;
in which the folder can be oriented around an adjustment axis arranged near the second guide and lying in the receiving plane, in order to vary a position of the first end of said elongated edge with respect to the first guide, so as to adjust a mutual position of opposite longitudinal edges of the web material at the second guide.

In accordance with a second aspect, the present invention relates to a method for folding web material in a process for producing layered composite articles, comprising:
feeding a web material along a feed direction and from a first guide defining a feeding plane for feeding the web material towards a second guide defining a receiving plane for receiving the web material, in which the second guide is positioned downstream of the first guide with respect to the feed direction, in which the receiving plane is substantially orthogonal to the feeding plane;
placing an intermediate portion of the web material in contact with an elongated edge of a folder arranged between the first guide and the second guide;
moving the intermediate portion of the web material along the receiving plane and away from the feeding plane and from opposite longitudinal edges of said web material, by sliding the intermediate portion on the elongated edge as it travels from the first guide towards the second guide, so as to fold said web material in two;
orienting the folder around an adjustment axis arranged near the second guide and lying in the receiving plane, in order to vary a position of a first end of said elongated edge with respect to the first guide so as to adjust a mutual position of the opposite longitudinal edges after the folding.

In accordance with one aspect, the present invention relates to a plant for producing layered composite articles, comprising:
a plurality of reel-carriers for respective reels of webs of material (such as, for example, polyethylene, non-woven fabric, cellulose wadding);
a plurality of conveyor and transmission devices defining respective paths for said webs of material;
a plurality of joining devices acting along said paths in order to join together said webs of material and possible further elements and form a layered composite web;
at least one cutting device for cutting said layered composite web and forming layered composite articles;
in which the plant also comprises the device in accordance with the first aspect and/or in accordance with one or more of the following aspects;
in which the web material folded by said device is one of the webs of material and/or the layered composite web.

In accordance with one aspect, the present invention relates to a process for producing layered composite articles, comprising:
feeding webs of material (such as, for example, polyethylene, non-woven fabric, cellulose wadding) along respective paths;
associating and joining together said webs of material and possibly further elements in order to form a layered composite web;
cutting said layered composite web in order to form layered composite articles;
in which the process also comprises the method in accordance with the second aspect and/or in accordance with one or more of the following aspects;
in which the web material of said method is one of the webs of material and/or the layered composite web.

With intermediate portion it is intended a longitudinal portion situated between the two opposite longitudinal edges. Such intermediate portion can more or less coincide with a middle line portion of the web material equidistant from the two longitudinal edges. If said intermediate portion coincides with the middle line portion, then the web is folded in half and the two longitudinal edges are mutually aligned, i.e. placed at a same height so as to mate after the folding. If said intermediate portion is different from the middle line portion, then the two longitudinal edges are positioned at different heights after the folding.

The Applicant has verified that the solution according to the invention first of all allows mutually positioning with precision the opposite longitudinal edges of the web material after the folding, preferably ensuring the alignment between said opposite longitudinal edges after the folding, and hence improving the quality of the layered composite articles obtained therefrom.

In fact the Applicant has verified that, by moving the first end of the elongated edge of the folder with respect to the first guide and thus also with respect to the intermediate portion, preferably with respect to the middle line, of the portion of web material which is arranged on the first guide, it is possible to compensate for the displacement of the intermediate portion of said web material, due to deformations and/or sliding of the same, more downstream, in a manner so as to mate said intermediate portion with the elongated edge at the second guide and hence ensure the desired mutual position, preferably the mutual alignment, of the opposite longitudinal edges of the web material downstream of the folder.

In other words, a rotation of the folder around the adjustment axis translates into a relative displacement of the opposite longitudinal edges of the web material folded in two, preferably in half.

The Applicant has in particular verified that the solution according to the invention allows aligning with precision the zones of the web material that must be mutually joined and hence making junctions, preferably welds, that are correct and high quality.

The Applicant has therefore verified that the solution according to the invention is simple and effective.

The Applicant has therefore verified that the solution according to the invention more generally allows improving the quality, also aesthetic, of the produced layered composite articles.

The Applicant has also verified that the solution according to the invention can be easily adapted to articles with different sizes and with characteristics different from each other.

The Applicant has also verified that the mechanical solution according to the invention is also structurally simple, inexpensive and easy to manage and maintain.

Further aspects of the invention are described hereinbelow.

In one aspect, the feeding plane is a substantially horizontal plane.

In one aspect, the feeding plane is tilted with respect to a horizontal plane by an angle comprised between 0° and 15°.

In one aspect, the receiving plane is a substantially vertical plane.

In one aspect, the adjustment axis forms, with a vertical direction, an angle comprised between 0° and 15°.

In one aspect, the elongated edge is directed downward.

In one aspect, the elongated edge has a curvilinear progression.

In one aspect, said curvilinear progression has a convexity directed downward.

In one aspect, a distance of the elongated edge from the opposite longitudinal edges of the web material, measured in the receiving plane, increases starting from the first guide towards the second guide.

In one aspect, a first end of the elongated edge is close to the first guide and a second end of the elongated edge is close to the second guide.

In one aspect, a first end of the elongated edge faces the first guide.

In one aspect, the first guide comprises a first transport surface at least partly parallel to the feeding plane.

In one aspect, the first transport surface is motorized.

In one aspect, the web material is arranged on the first transport surface.

In one aspect, the first guide comprises a first roller, in which the first transport surface is a radially external surface of the first roller.

In one aspect, the first roller has a rotation axis parallel to the feeding plane.

In one aspect, the first guide comprises a first conveyor belt, in which the first transport surface is a surface of said first conveyor belt.

In one aspect, the second guide comprises second transport surfaces that are opposite and parallel to the receiving plane.

In one aspect, the second transport surfaces are motorized.

In one aspect, the web material folded in two, preferably in half, is arranged between the second transport surfaces.

In one aspect, a second end of the elongated edge is arranged between the second transport surfaces.

In one aspect, the second guide comprises a pair of opposite second rollers, in which the second transport surfaces are radially external surfaces of the second rollers.

In one aspect, the opposite second rollers have rotation axes parallel to the receiving plane.

In one aspect, the second guide comprises a pair of second conveyor belts, in which the second transport surfaces are surfaces of said second conveyor belts.

In one aspect, the folder comprises a substantially flat body mainly extended in the receiving plane.

In one aspect, the elongated edge is a lower edge of said substantially flat body.

In one aspect, the folder can be oriented around the adjustment axis by an angle comprised between +/−15°, preferably comprised between +/−10°, with respect to an average position corresponding to a mid-point of the first guide.

In one aspect, the folder can be oriented around the adjustment axis by an angle comprised between +/−15°, preferably comprised between +/−10°, with respect to a middle line portion of the section of web material placed on the first guide.

In one aspect, the folder is hinged to a support around said adjustment axis.

In one aspect, the folder is hung from said support.

In one aspect, the folder comprises an arm having one end connected to the substantially flat body and an opposite end hinged to said support around the adjustment axis.

In one aspect, the adjustment axis passes through the, or near the, second end of the elongated edge.

In one aspect, an actuator is connected to the folder, preferably to the substantially flat body, and is configured for moving said folder around the adjustment axis.

In one aspect, the actuator is connected to the folder near the first end.

In one aspect, the actuator is a linear actuator.

In one aspect, the actuator is of screw/nut screw type.

In one aspect, the folder is manually moved around the adjustment axis.

In one aspect, the actuator is manually actuated, for example by means of a thrust lever.

In one aspect, locking devices are configured for locking the folder in the desired position.

In one aspect, the actuator is of electrical, pneumatic or hydraulic type.

In one aspect, the actuator comprises a rod having one end hinged to the folder and an opposite end hinged to a fixed frame of the device and/or of the plant.

In one aspect, at least one position sensor is configured for detecting a position, preferably relative position, of the opposite longitudinal edges of the web material.

In one aspect, said at least one position sensor is mounted at the second end of the folder, preferably of the substantially flat body.

In one aspect, said at least one position sensor is mounted alongside the folder, preferably alongside the substantially flat body.

In one aspect, said at least one position sensor is mounted integral with the fixed frame of the device and/or of the plant.

In one aspect, said at least one position sensor is of optical or ultrasound type.

In one aspect, said at least one position sensor comprises a video camera.

In one aspect, said at least one position sensor comprises two position sensors, each position sensor being arranged on a respective side of the folder, preferably of the substantially flat body, in order to spot a respective longitudinal edge of the web material that is at least partly folded.

In one aspect, a position of the position sensor(s) is adjustable.

In one aspect, an electronic control unit is operatively connected to the actuator.

In one aspect, the electronic control unit is operatively connected to said at least one position sensor.

In one aspect, the electronic control unit is configured or programmed for executing the following procedure: receiving from said at least one position sensor at least one signal related to the position, preferably relative position, of the opposite longitudinal edges of the web material; controlling the actuator as a function of said at least one signal up to mutually positioning the opposite longitudinal edges in a desired position, preferably up to mutually aligning the opposite longitudinal edges.

In one aspect, it is provided to detect a misalignment between the opposite longitudinal edges and orient the folder so as to eliminate said misalignment.

In one aspect, it is provided to detect a misalignment between the opposite longitudinal edges and orient the folder up to obtaining a predetermined and desired misalignment.

In one aspect, the electronic control unit is configured or programmed for executing the following procedure: receiving, from each of the two position sensors, a respective signal; calculating a difference between the two signals.

In one aspect, the electronic control unit is configured or programmed for executing the following procedure: controlling the actuator in order to rotate the folder around the adjustment axis up to obtaining a predetermined and desired misalignment.

In one aspect, the electronic control unit is configured or programmed for executing the following procedure: controlling the actuator in order to rotate the folder around the adjustment axis if said difference is non-zero.

In one aspect, the electronic control unit is configured or programmed for executing the following procedure:
controlling the actuator in order to rotate the folder around the adjustment axis in one sense if said difference is greater than zero; or
controlling the actuator in order to rotate the folder around the adjustment axis in an opposite sense if said difference is less than zero.

In one aspect, in order to eliminate said misalignment, it is provided to rotate the folder towards the longitudinal edge placed further away from the elongated edge of the folder.

In one aspect, while the opposite longitudinal edges of the web material advance in the feed direction, said opposite longitudinal edges approach each other.

In one aspect, after having brought the opposite longitudinal edges of the web material close to each other, it is provided to associate portions to be mutually joined and join together said portions, preferably by means of welding.

In one aspect, while the opposite longitudinal edges of the web material advance in the feed direction, said longitudinal edges are maintained at a higher elevation with respect to the intermediate portion, preferably with respect to the middle line portion.

In one aspect, the web material is a layered composite web.

In one aspect, the layered composite articles are pull-up diapers.

In one aspect, the web material comprises a plurality of layered composite articles joined together in series and, preferably, configured for making pull-up diapers.

In one aspect, the intermediate portion, preferably middle line portion, of the layered composite web corresponds with a crotch of the pull-up diapers.

In one aspect, the opposite longitudinal edges of the layered composite web correspond with the waist of the pull-up diapers.

In one aspect, the portions to be mutually joined correspond with the sides of each pull-up diaper.

In one aspect, the folder comprises a motorized conveyor arranged along the elongated edge, movable from the first guide towards the second guide and configured for accompanying and/or driving the intermediate portion, preferably middle line portion, of the web material along said elongated edge.

In one aspect, moving the intermediate portion also comprises: accompanying and/or driving the intermediate portion of the web material from the first guide towards the second guide.

In one aspect, the motorized conveyor comprises a transport belt extended at least partly along the elongated edge.

In one aspect, the motorized conveyor comprises a plurality of pulleys.

In one aspect, the transport belt is wound on said pulleys.

In one aspect, the substantially flat body comprises two side-by-side plates delimiting a housing between them for the transport belt.

In one aspect, it is provided to adjust a speed of the motorized conveyor, preferably of the transport belt, preferably of a branch of the transport belt arranged along the elongated edge.

In one aspect, actively accompanying and/or driving the intermediate portion, preferably middle line portion, comprises: adjusting or maintaining a relative position between the waist and the crotch of each of the pull-up diapers while the web material is folded.

The Applicant has verified that the motorized conveyor prevents the intermediate portion from remaining behind with respect to the opposite longitudinal edges of the web material. Indeed, the motorized conveyor is moved together with the intermediate portion and accompanies/drives it towards the second guide, maintaining the web material substantially undeformed.

Further characteristics and advantages will be clearer from the detailed description of a preferred but not exclusive embodiment of a device and of a method for folding web material in a plant for producing layered composite articles, in accordance with the present invention.

BRIEF DESCRIPTION OF THE DRAWINGS

Such description will be set forth hereinbelow with reference to the enclosed drawings, provided merely as a non-limiting example in which:

FIG. 11 is a flow diagram of the method according to the present invention.

DETAILED DESCRIPTION OF PREFERRED EMBODIMENTS OF THE INVENTION

Figure 1:
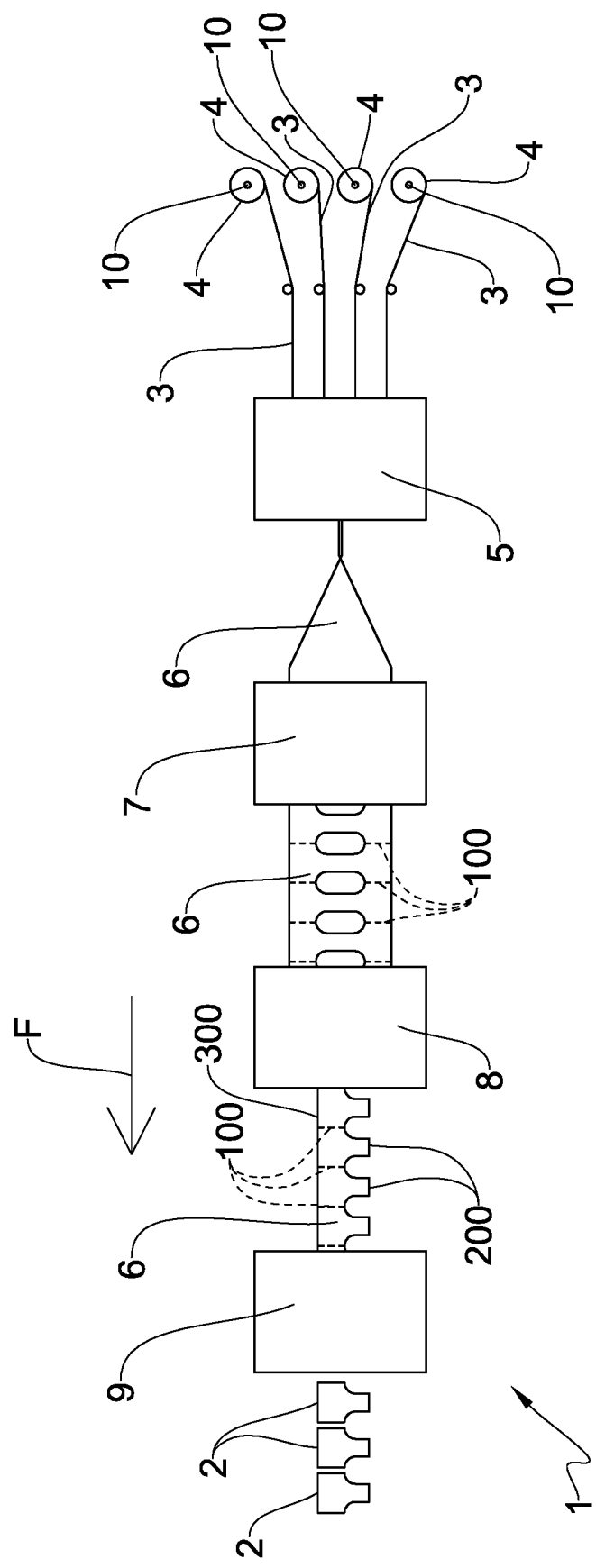
FIG. 1 shows a schematic view of a plant for producing layered composite articles according to the present invention.

With reference to the enclosed figures, reference number 1 overall indicates a manufacturing plant for producing layered composite articles 2. The plant 1, illustrated as preferred embodiment, is configured for producing pull-up diapers 2. In other non-illustrated embodiments, the plant 1 can be configured for producing other types of sanitary articles or clothing articles or accessories.

In the plant 1, the packaging of the abovementioned layered composite articles 2 is executed starting from different semi-finished products, including webs of material 3 wound in reels 4, such as polyethylene, non-woven fabric, cellulose wadding (tissue), etc.

The webs of material 3 are continuously fed through the plant 1 along respective paths and are joined, shaped, adapted and cut, etc., in order to give rise to the abovementioned layered composite articles 2.

In the schematic example illustrated in FIG. 1, the plant 1 comprises a first sector 5 along which the webs of material 3 are joined together to form a continuous semi-finished product constituted by a layered composite web 6 fed along a transport direction "F". The layered composite web 6 is rotated 90° while it advances towards a second sector 7 in which it is cut/shaped. In a third sector 8, the layered composite web 6 is folded in two along a longitudinal line and then, in a fourth sector 9, welds are executed and the single articles/diapers 2 are separated from each other.

The plant 1 comprises a plurality of reel-carriers 10 for the respective reels 4 of webs of material 3. The first sector 5 is provided with conveyor and transmission devices which define respective paths for said webs of material 3 and joining/gluing devices acting along said paths in order to join together said webs of material 3 and with further elements and form the layered composite web 6. The second sector 7 comprises conveyor and transmission devices for the layered composite web 6 and cutting and shaping devices. The third sector 8 comprises a device 11 for folding web material, illustrated in detail hereinbelow, and one or more welding stations. The fourth sector 9 comprises at least one cutting device configured for cutting said folded layered composite web 6 and separating the layered composite articles 2 (pull-up diapers) from each other.

The layered composite web 6 coming from the second sector 7 and directed towards the third sector 8 is constituted by a plurality of pull-up diapers 2 that are open and already shaped following the leg opening operation, i.e. creation of the openings for the legs.

The layered composite web 6 coming from the third sector 8 and directed towards the fourth sector 9 is constituted by the plurality of pull-up diapers 2 that are closed and welded at the sides but still joined in series with each other. The following are visible: the dashed lines 100 (FIGS. 1 and 4) along which the crotch 200 and the waist 300 of each diaper 2 will be cut in order to separate them. The dashed lines 100 also indicate the welded zones at the sides of each diaper 2.

The device for folding web material 11 (FIG. 2) comprises a first guide defined by a first roller 12 rotatable around a horizontal rotation axis "X-X" thereof and preferably connected to a motor, not illustrated and configured for rotating it around said rotation axis "X-X". An upper portion of a radially external surface of the first roller 12 defines a first transport surface for the layered composite web 6 coming from the second sector 7. The layered composite web 6 is partially wound on the abovementioned radially external surface of the first roller 12.

In an alternative, non-illustrated embodiment, the first guide can comprise a first conveyor belt partially wound around the first roller 12.

A second guide comprising a pair of opposite second conveyor belts 13 wound on respective opposite second rollers 14 (more visible in FIG. 4) is situated downstream of the first roller 12 and is spaced therefrom. The second rollers 14 are preferably motorized and rotate around respective rotation axes "Y-Y" lying in vertical planes. Internal branches of the second conveyor belts 13 define second transport surfaces for the layered composite web 6. The rotation axes "Y-Y" of the second rollers 14 are tilted with respect to a vertical direction by an angle of about 5°, so that the second conveyor belts 13 are moved along a feed direction "V" tilted by about 5° with respect to a horizontal direction.

In a non-illustrated embodiment variant, the conveyor belts 13 are absent and the second transport surfaces are radially external surfaces of the second rollers 14.

The second guide is therefore placed downstream of the first guide with respect to the feed direction "V" of the layered composite web 6.

The first guide defines a feeding plane for feeding the layered composite web 6 which leaves the first roller 12. Such feeding plane is tilted by the abovementioned angle of about 5° and it is also the plane in which the layered composite web 6 lies immediately downstream of the first roller 12. The rotation axis "X-X" of the first roller 12 is parallel to the feeding plane.

The second guide defines a receiving plane for receiving the layered composite web 6. Such receiving plane is vertical and is parallel to the and interposed between the second transport surfaces of the second conveyor belts 13. The receiving plane is therefore orthogonal to the feeding plane.

A folder 15 is arranged between the first guide and the second guide and is configured for folding in two the layered composite web 6 along an intermediate portion thereof.

In the illustrated non-limiting embodiment, the folder 15 is arranged between the first guide and the second guide and is configured for folding in half the layered composite web 6 along a longitudinal middle line portion 16 thereof and for approaching opposite longitudinal edges 17 of said layered composite web 6 while the layered composite web 6 continuously moves from the first guide towards the second guide along the abovementioned feed direction "V".

Figure 2:
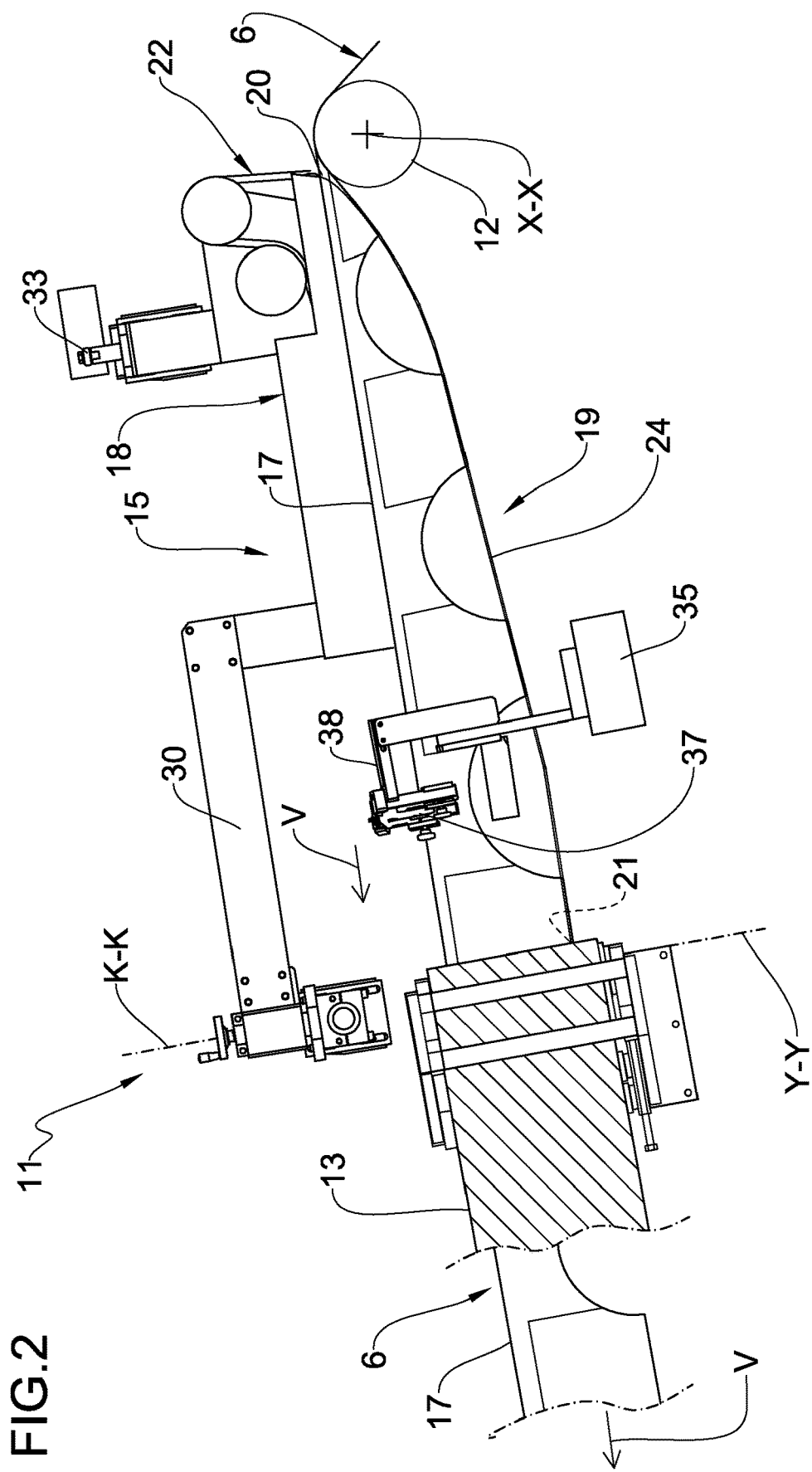
FIG. 2 shows, in a side view, several elements of a station of the plant of FIG. 1 coupled with a web material.
Figure 3:
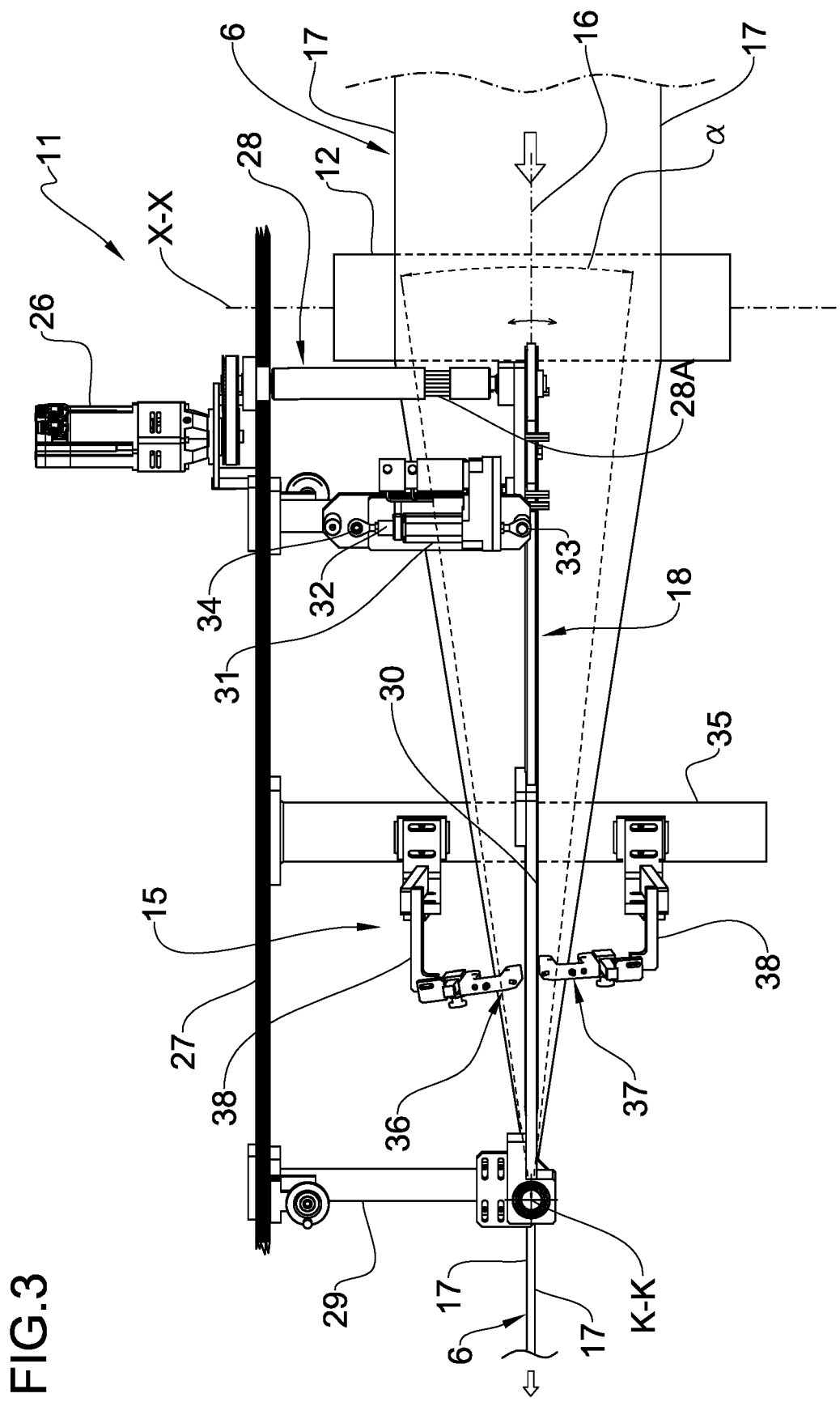
FIG. 3 is a top view of the station of FIG. 2.
Figure 4:
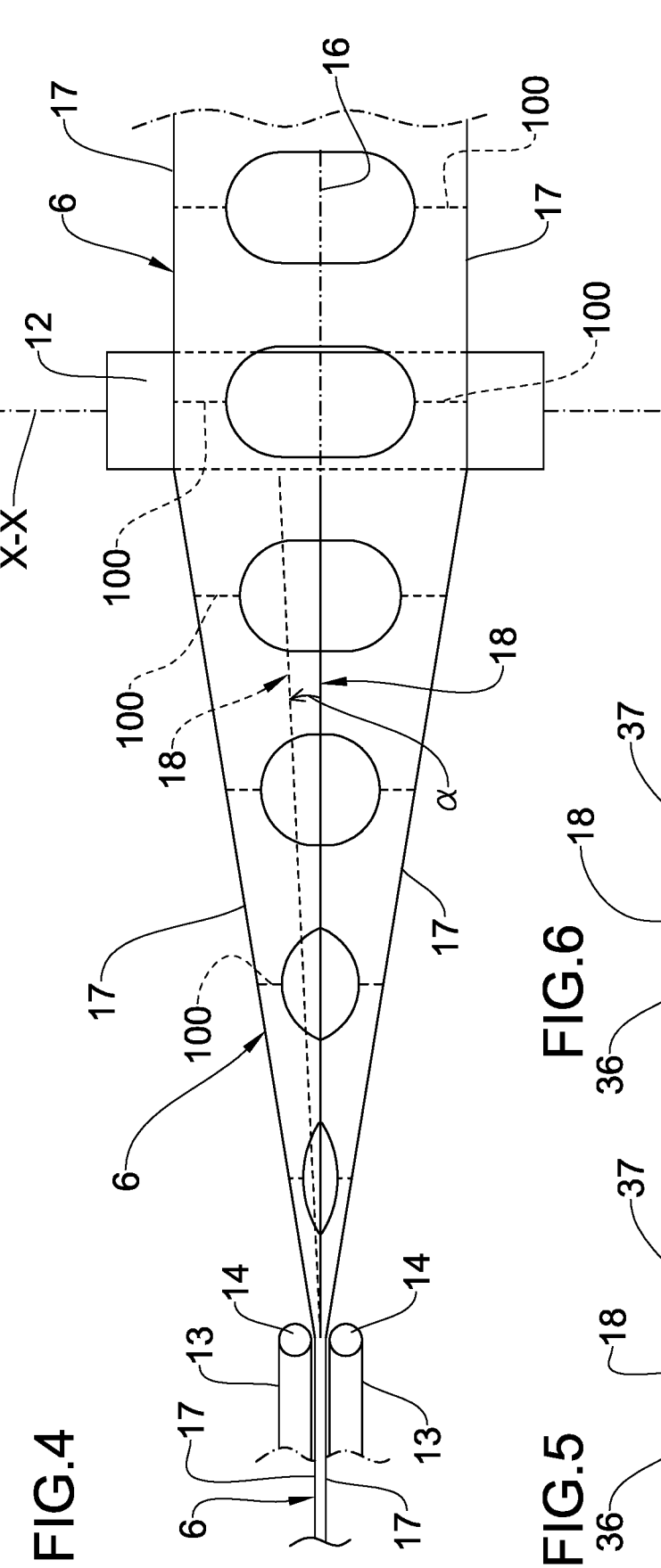
FIG. 4 schematically illustrates a step for folding the web material executed in the station of FIGS. 2 and 3.

As is visible in FIGS. 2, 3 and 4, the layered composite web 6 lies open in the feeding plane when it is situated just downstream of the first roller 12 and is folded in two when it is situated between the second transport surfaces of the second conveyor belts 13.

The folder 15 comprises a substantially flat body 18 defined by two side-by-side plates delimiting a housing between them. The substantially flat body 18 is situated in a vertical plane, i.e. substantially in the receiving plane.

A lower elongated edge 19 of the substantially flat body 18 is extended between the first guide and the second guide and has a first end 20 close to the first guide and a second end 21 close to the second guide. The elongated edge 19 has a curvilinear progression with a convexity directed downward. The first roller 12 partly lies below the first end 20 of the elongated edge 19 and such first end 20 faces the radially external surface of the first roller 12. The second end 21 of the elongated edge 19 terminates between the second rollers 14.

Figure 7:
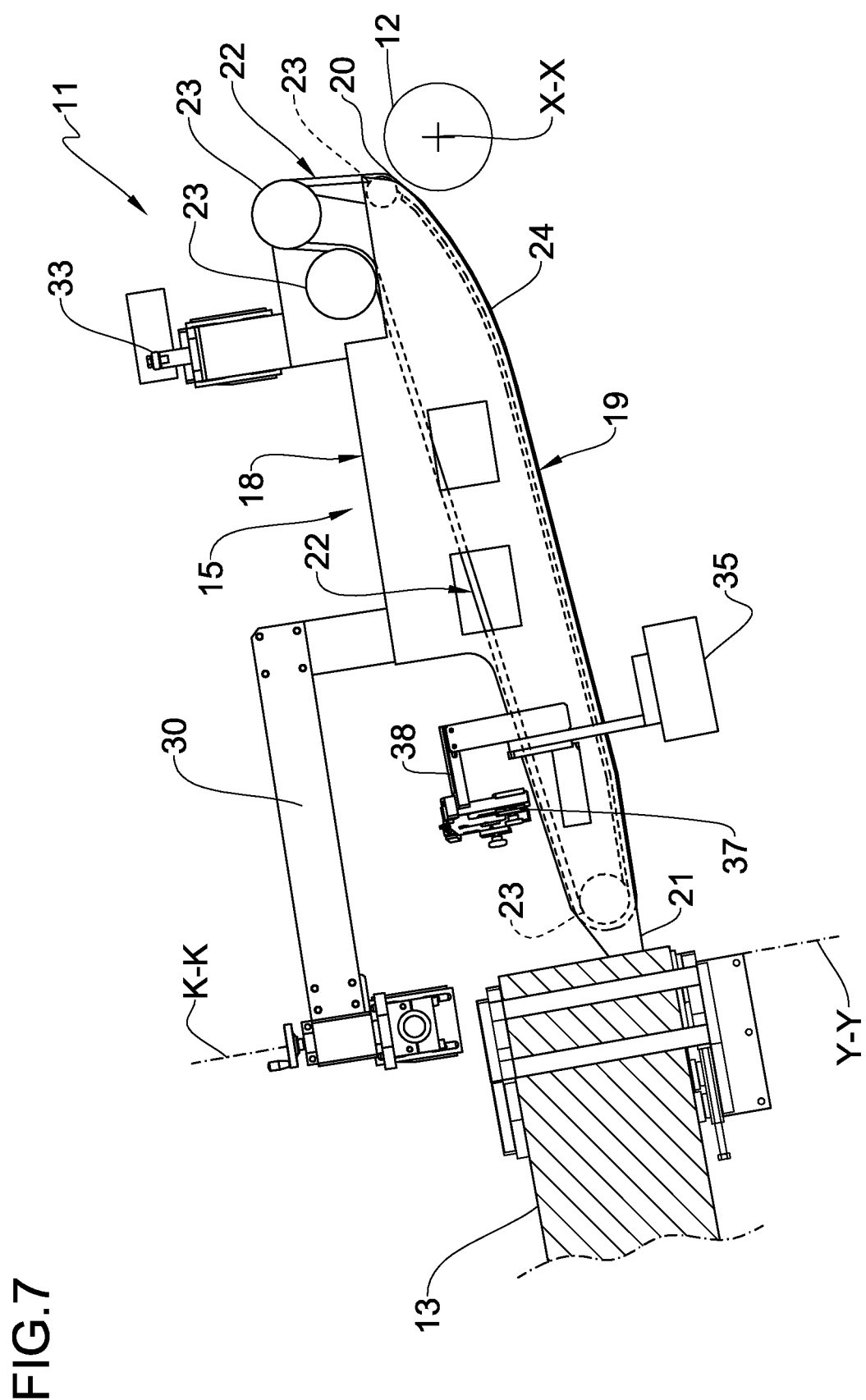
FIG. 7 is a further side view of the elements of FIG. 2.
Figure 8:
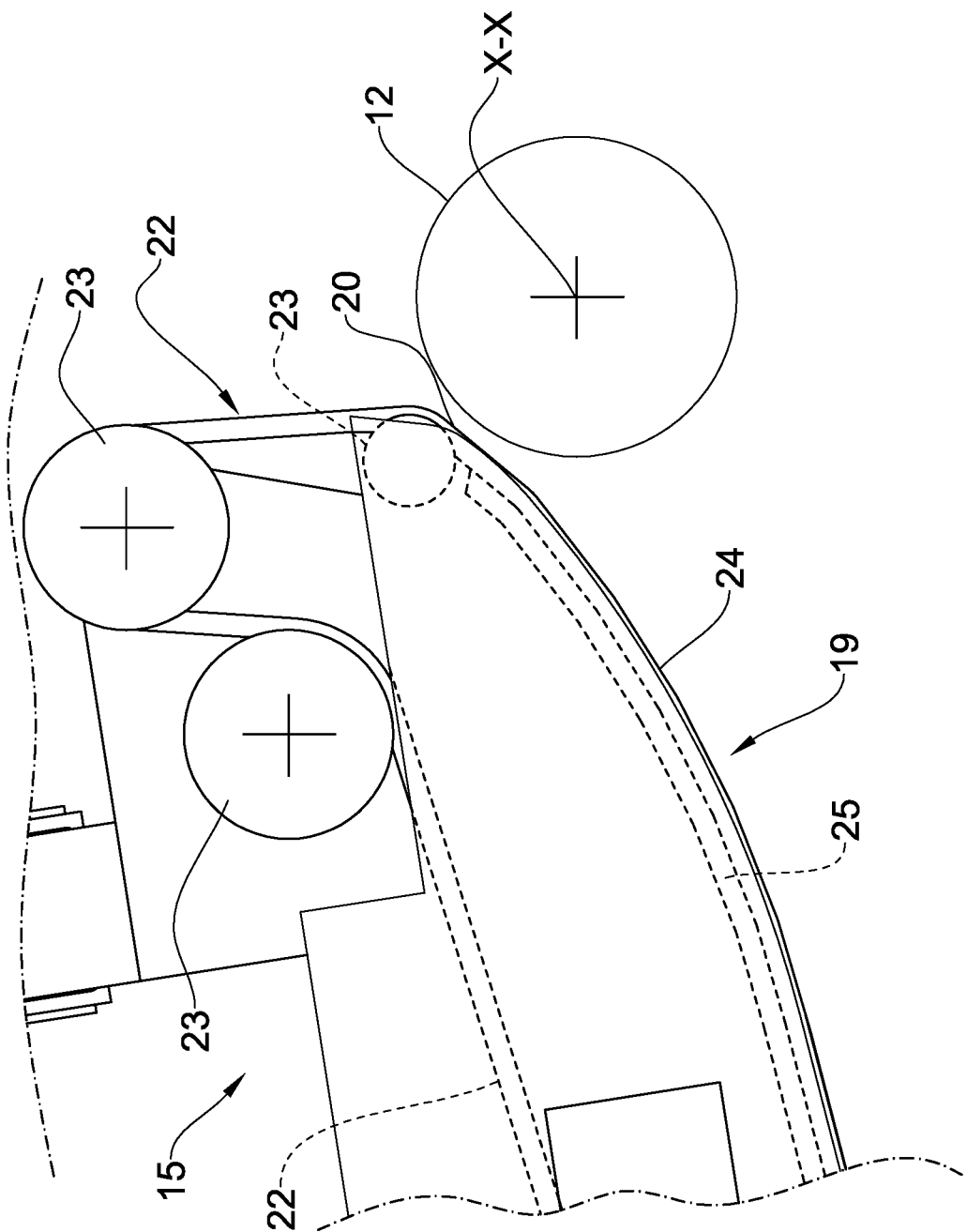
FIG. 8 is an enlargement of a part of FIG. 7.
Figure 9:
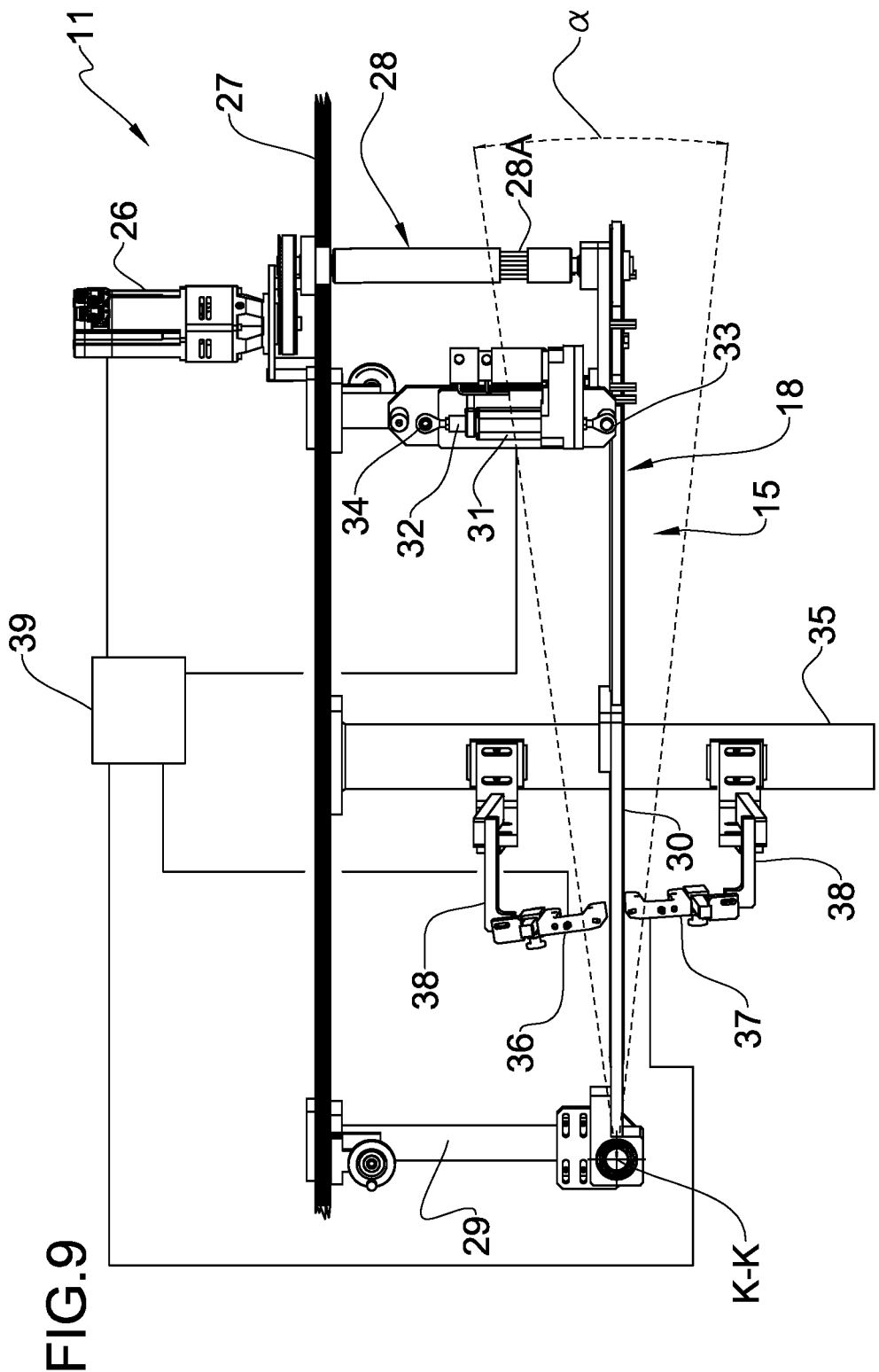
FIG. 9 is a further top view of the station of FIG. 3.

As is visible in FIGS. 2, 7 and 8, the elongated edge 19 has a first part, close to the first end 20, with a greater curvature which is extended downward, followed by a second part with lesser curvature and by a third substantially rectilinear part that terminates in the second end 21. The elongated edge 19 is therefore extended from the first guide towards the second guide in the receiving plane and progressively downward, i.e. away from the feeding plane. A distance of the elongated edge 19 from the opposite longitudinal edges 17 of the web 6, measured in the receiving plane, increases starting from the first guide towards the second guide.

A transport belt 22, e.g. made of rubber or polyurethane, is wound on pulleys 23 and situated in the housing delimited between the two side-by-side plates. The pulleys 23 are rotatably mounted between the abovementioned two plates and are provided with teeth. The transport belt 22 is for example toothed and teeth of said belt 22 are engaged with the pulleys 23. Other types of belts can be used, for example, flat belts, polycord belts, trapezoidal belts etc.

The transport belt 22 is extended along a closed path substantially lying in the receiving plane. A lower branch 24 of the transport belt 22 is arranged along the elongated edge 19 and projects from said elongated edge 19. A guide element 25 is mounted between the two side-by-side plates and the lower branch 24 can slide against this. In place of the guide element 25, a plurality of small rollers can be present, not illustrated.

One of the pulleys 23 is motorized, i.e. it is connected to a motor 26, in order to rotate said pulley 23 and move the transport belt 22 along the closed path. A motion sense of the transport belt 22 along the closed path is such to move the branch 24 from the first guide towards the second guide.

The transport belt 22, together with the pulleys 23, with the guide 25 and with the motor 26 therefore defines a motorized conveyor, arranged along the elongated edge 19 and movable from the first guide towards the second guide.

In the illustrated embodiment, the motor 26 is mounted on a fixed frame 27 of the plant 1 defined by a vertical wall. The folder 15 is spaced from said vertical wall and the motor 26 is connected to the pulley 23 placed above the first end 20 of the elongated edge 19 by means of a Cardan shaft 28 which is extended from the motor 26 and from said vertical wall up to the pulley 23.

The folder 15 is hinged to and hung from a support 29 around an adjustment axis "K-K". The support 29 is a bar which is extended cantilevered from the vertical wall and bears a pivot, in order to rotatably connect the folder 15, placed at a terminal end thereof. The folder 15 comprises an arm 30 which has one end integrally connected to the substantially flat body 18 and an opposite end hinged to said support 29 around the adjustment axis "K-K". The arm 30 is substantially extended parallel to the feed direction "V" and the opposite end is joined to an intermediate zone of the substantially flat body 18.

The adjustment axis "K-K" passes near the second end 21 of the elongated edge 19, is orthogonal to the feed direction "V" and lies in a vertical plane, i.e. in the receiving plane. The adjustment axis "K-K" forms, with a vertical direction, an angle of about 5°.

The folder 15 can be oriented around the abovementioned adjustment axis "K-K", in order to vary a position of the first end 20 of said elongated edge 19 with respect to the first roller 12, so as to adjust a mutual alignment of the opposite longitudinal edges 17 at the second conveyor belts 13.

An actuator 31 is connected to the substantially flat body 18 and is configured for moving the folder 15 around the adjustment axis "K-K". The actuator 31 is situated between the vertical wall and the substantially flat body 18. In particular, the actuator 31 is a linear actuator (e.g. electric, screw/nut screw type, pneumatic or hydraulic) and has a rod 32 provided with one end 33 hinged to the folder 15 (or to an element integral with the folder 15) and with an opposite end 34 hinged to the fixed frame 27 (or to an element integral with the fixed frame 27). The end 33 hinged to the folder 15 is situated at the first end 20 of the elongated edge 19, i.e. at the Cardan shaft 28.

The travel of the rod 32 is such to allow orienting the folder 15 around the adjustment axis "K-K" by an angle "a" comprised between +/−15°, preferably comprised between +/−10°, with respect to an average position in which the substantially flat body 18 is parallel to the wall 27 and the first end 20 of the elongated edge 19 faces a mid-point of the first roller 12, i.e. to the middle line portion 16 of the web section 6 placed on the first roller 12.

Figure 10:
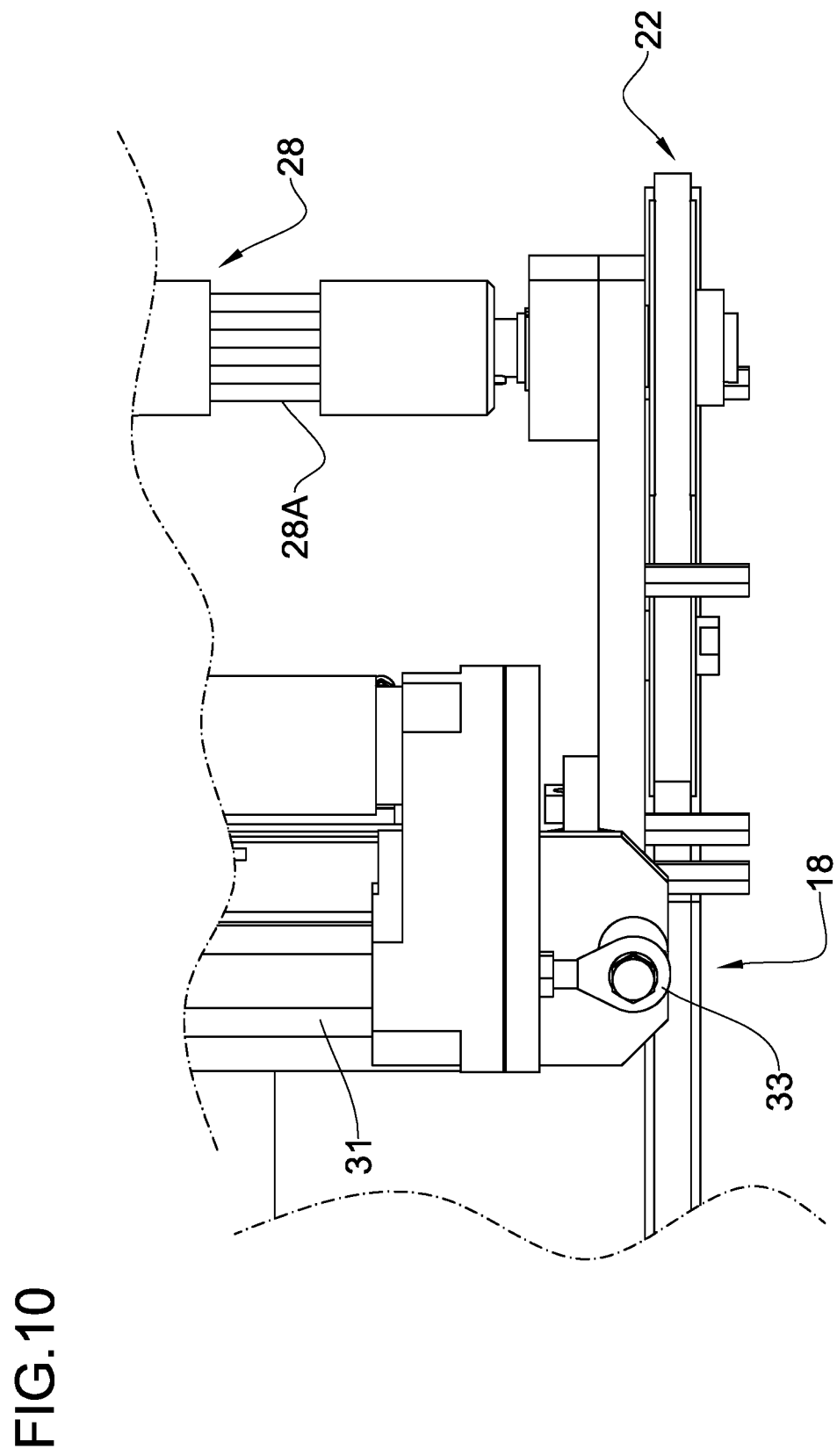
FIG. 10 is an enlargement of a part of FIG. 9.

The Cardan shaft 28 allows the folder 15 to oscillate as illustrated around the adjustment axis "K-K" due to a slidable coupling 28A between two parts of the same shaft 28 (FIG. 10). Such coupling is for example of splined type in order to prevent the rotation between said two parts.

The device 1 for folding web material also comprises two position sensors of optical type, each position sensor being arranged on a respective side of the folder 15. The position sensors are mounted on a respective support bar 35 which projects from the wall 27, is integral with the wall 27 itself and is situated below the folder 15. The two position sensors are positioned near the second guide, i.e. the second conveyor belts 13.

A first position sensor 36 of said two position sensors is situated between the wall 27 and the substantially flat body 18. A second position sensor 37 of said two position sensors is situated on a side opposite the substantially flat body 18.

Each of the two position sensors is mounted on a respective small arm 38 in turn mounted on the support bar 35 and such small arm 38 allows an adjustment of the position of the respective sensor.

Each of the abovementioned sensors 36, 37 comprises an emitter and an optical receiver that are mutually facing and spaced from each other in a manner such that one of the opposite longitudinal edges 17 can slide between the emitter and the receiver.

The two position sensors are configured for detecting a relative position of the two opposite longitudinal edges 17 of the layered composite web 6, in particular a height of said two opposite longitudinal edges 17. For example, the two position sensors are configured for supplying a differential signal that is a function of the difference of the height position of the two opposite longitudinal edges 17.

In other embodiments, not illustrated, different sensors can be provided, for example video cameras or ultrasound sensors or still more.

An electronic control unit 39 is operatively connected to the motor 26 of the motorized conveyor, to the non-illustrated motor which moves the first roller 12 and to the non-illustrated motor which moves the pair of conveyor belts 13. The electronic control unit 39 is also operatively connected to the actuator 31 and to the first and second position sensor 36, 37.

Such electronic control unit 39 is for example the electronic control unit of the entire plant 1.

During use and in accordance with the present invention (FIG. 11), the layered composite web 6, which lies open in the feeding plane when it is situated just downstream of the first roller 12, encounters the first end 20 of the elongated edge 19. Said elongated edge 19 comes into contact with the middle line portion 16 of the layered composite web 6 and, while the web 6 advances towards the second guide, moves the middle line portion 16 downward while the opposite longitudinal edges 17 continue the rectilinear movement thereof. The middle line portion 16 is progressively moved away from the feeding plane while the opposite longitudinal edges 17 are maintained at a higher elevation with respect to the middle line portion 16 and they progressively approach each other. In this manner, the layered composite web 6 is progressively folded in half.

In particular, the middle line portion 16 comes into contact with the branch 24 of the transport belt 22 and is accompanied or driven by the branch 24 towards the second guide. In other words, the middle line portion 16 is moved together with the branch 24 without sliding on the elongated edge 19.

By manually or automatically adjusting (e.g. by means of the electronic control unit 39) a power delivered by the motor 26 and hence a speed of the transport belt 22, i.e. a driving speed for the middle line portion 16, it is possible to prevent the middle line portion 16 from remaining behind with respect to the opposite longitudinal edges 17 of the layered composite web 6 and hence prevent said layered composite web 6 from being deformed.

Since the middle line portion 16 corresponds with the crotch 200 of the pull-up diapers 2 and the opposite longitudinal edges 7 correspond with the waist 300 of the pull-up diapers 2, the adjustment of the speed of the transport belt 22 allows maintaining an alignment between the waist 300 and the crotch 200 of each pull-up diaper 2 and preventing the deformation of the single diapers 2 before the welding of the sides.

According to one embodiment, it is sufficient to set the speed of the motorized conveyor at the start of a production batch, as a function of a speed of the plant 1 and in particular of a speed of the first roller 12 and of a speed of the second conveyor belts 13 and/or of characteristics/dimensions of the pull-up diapers 2 to produce, such that the abovementioned alignment is maintained.

The electronic control unit 39 receives, from each of said first and second position sensor 36, 37, a respective signal as a function of a position of a section of a respective opposite longitudinal edge 17 of the layered composite web 6 when this is situated just before the second conveyor belts 13. In such position, the folding step is nearly complete, the layered composite web 6 is arranged as a V and the two abovementioned opposite longitudinal edges 17 are close to each other even if they do not touch (FIGS. 5 and 6).

The electronic control unit 39 calculates a difference between the two signals. Such difference is a function of a height difference "Δh" (misalignment) of the two opposite longitudinal edges 17 (FIG. 5). If such difference is non-zero, this signifies that the middle line portion 16 of the layered composite web 6 is moved laterally with respect to the elongated edge 19, as in FIG. 5.

If said difference is non-zero, the electronic control unit 39 is programmed for controlling the actuator 31 so as to rotate the folder 15 around the adjustment axis "X-X" by an angle "a" and in a sense such to bring the two opposite longitudinal edges 17 to a same height and hence cancel the abovementioned height difference "Δh". The electronic control unit 39 is programmed for rotating the folder 15 towards the longitudinal edge 17 placed higher and by an angle proportional to the detected height difference "Δh".

Figure 5:
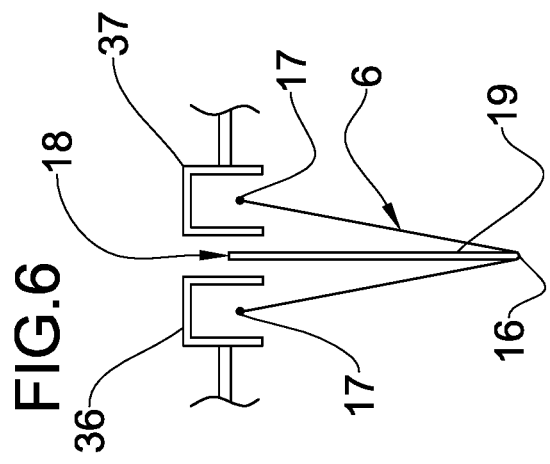
FIGS. 5 and 6 illustrate respective configurations for folding the web material executed in the station of FIGS. 2 and 3.
Figure 6:
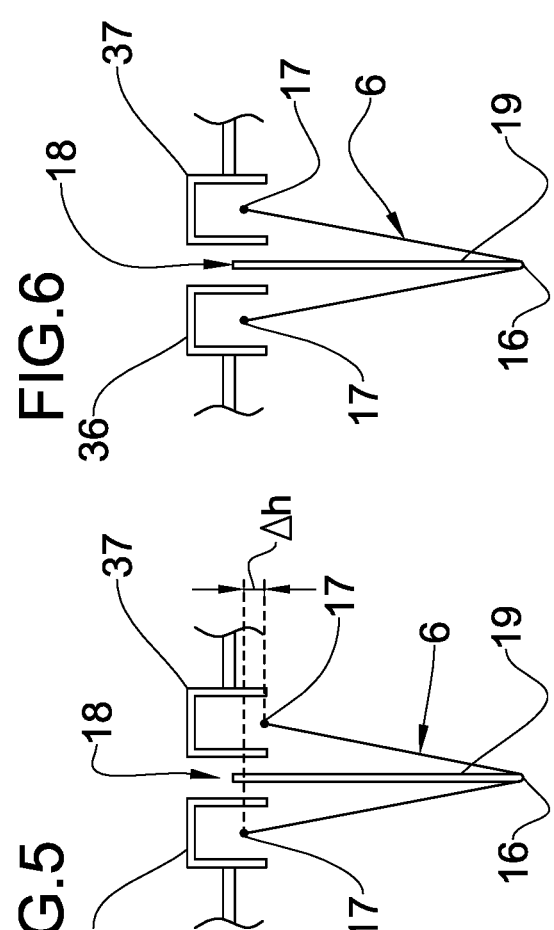

For example, with reference to FIGS. 4, 5 and 6, if the longitudinal edge 17 placed at the first position sensor 36 is placed higher than the longitudinal edge 17 placed at the second position sensor 37 (as in FIG. 5), the folder 15 is rotated towards the wall 27 in order to move the first end 20 of the longitudinal edge 19 towards said wall 27 and in this manner lift the longitudinal edge 17 placed at the second position sensor 37 and lower the other, up to aligning the two edges (FIG. 6) with each other.

The opposite longitudinal edges 17 of the layered composite web 6 are therefore aligned with each other when they enter between the second conveyor belts 13 and, in this manner, the zones belonging to the two opposite longitudinal edges 17 and to be welded together mate with precision.

Downstream of the second conveyor belts 13, the welding stations provide for executing the welds correctly.

In other embodiments not illustrated in detail, the folder is manually moved around the adjustment axis by actuating, by means of a thrust lever, the actuator which for example is of screw/nut screw type, and it is then locked in the desired position by means of suitable locking devices. In such case, the position of the opposite longitudinal edges of the web material is visually controlled by an operator or it can be provided on a display by the control unit connected to the abovementioned sensors.

ELEMENTS

1 Manufacturing plant for producing layered composite articles
2 Layered composite article/pull-up diapers
3 Web of material
4 Reel
5 First sector
6 Layered composite web
7 Second sector
8 Third sector
9 Fourth sector
10 Reel-carrier
11 Device for folding web material
12 First roller
13 Pair of conveyor belts
14 Second rollers
15 Folder
16 Middle line portion
17 Opposite longitudinal edges
18 Substantially flat body
19 Elongated edge
20 First end of the elongated edge
21 Second end of the elongated edge
22 Transport belt
23 Pulleys
24 Branch of the transport belt
25 Guide element
26 Motor
27 Fixed frame
28 Cardan shaft
28A Slidable coupling
29 Support
30 Arm
31 Actuator
32 Rod
33 End of the rod
34 Opposite end of the rod
35 Support arm
36 First position sensor
37 Second position sensor
38 Small arms
39 Electronic control unit
100 Cutting lines
200 Crotch
300 Screw
F Transport direction
V Feed direction
X-X Rotation axis of the first roller
Y-Y Rotation axes of the second rollers

The invention claimed is:

1. Device for folding web material in a plant for producing layered composite articles comprising:
   a first guide defining a feeding plane for feeding a web material;
   a second guide defining a receiving plane for receiving the web material, wherein the second guide is positioned downstream of the first guide with respect to a feed direction of said web material, wherein the receiving plane is orthogonal to the feeding plane;
   a folder arranged between the first guide and the second guide and comprising an elongated edge extended between the first guide and the second guide and having a first end close to the first guide and a second end close to the second guide;
   wherein the elongated edge is extended from the first guide towards the second guide in the receiving plane and away from the feeding plane, in order to progressively move an intermediate portion of the web material away from the feeding plane and fold said web material in two as it travels from the first guide towards the second guide;
   wherein the folder can be oriented around an adjustment axis arranged near the second guide and lying in the receiving plane, in order to vary a position of the first end of said elongated edge with respect to the first guide so as to adjust a mutual position of opposite longitudinal edges of the web material at the second guide.

2. Device according to claim 1, wherein the folder can be oriented around the adjustment axis by an angle comprised between +/−10° with respect to an average position corresponding to a mid-point of the first guide.

3. Device according to claim 1, wherein the folder is hinged to a support around said adjustment axis.

4. Device according to claim 3, wherein the folder is hung from said support.

5. Device according to claim 3, wherein the folder comprises a substantially flat body mainly extended in the receiving plane and an arm having one end connected to the substantially flat body and an opposite end hinged to said support around the adjustment axis.

6. Device according to claim 1, comprising an actuator connected to the folder and configured for moving said folder around the adjustment axis.

7. Device according to claim 6, wherein the actuator is connected to the folder near the first end.

8. Device according to claim 6, comprising at least one position sensor configured for detecting a position of the opposite longitudinal edges of the web material.

9. Device according to claim 8, comprising an electronic control unit operatively connected to the actuator and to said at least one position sensor and configured or programmed for executing the following procedure:
   receiving, from said at least one position sensor, at least one signal related to the position of the opposite longitudinal edges of the web material;
   controlling the actuator as a function of said at least one signal up to mutually positioning the opposite longitudinal edges.

10. Method for folding web material in a process for producing layered composite articles, comprising:
    feeding a web material along a feed direction and from a first guide defining a feeding plane for feeding the web material towards a second guide defining a receiving plane for receiving the web material, wherein the second guide is positioned downstream of the first guide with respect to the feed direction, wherein the receiving plane is orthogonal to the feeding plane;
    placing an intermediate portion of the web material in contact with an elongated edge of a folder arranged between the first guide and the second guide;
    moving the intermediate portion of the web material along the receiving plane and away from the feeding plane and from opposite longitudinal edges of said web material, by sliding the intermediate portion on the elongated edge as it travels from the first guide towards the second guide, so as to fold said web material in two;
    orienting the folder around an adjustment axis arranged near the second guide and lying in the receiving plane, in order to vary a position of a first end of said elongated edge with respect to the first guide so as to adjust a mutual position of the opposite longitudinal edges after the folding.

11. Method according to claim 10, comprising: detecting a misalignment between the opposite longitudinal edges and orienting the folder until said misalignment is eliminated.

12. Method according to claim 10, comprising: detecting a misalignment between the opposite longitudinal edges and orienting the folder until a predetermined misalignment is obtained.

13. Method according to claim 10, wherein the web material comprises a plurality of layered composite articles joined together in series and configured for making pull up diapers; wherein the intermediate portion corresponds with a crotch of the pull up diapers; wherein the opposite longitudinal edges of the web material correspond with the waist of the pull up diapers.

14. Plant for producing layered composite articles, comprising:
    a plurality of reel-carriers for respective reels of webs of material;
    a plurality of conveyor and transmission devices defining respective paths for said webs of material;
    a plurality of joining devices acting along said paths in order to join together said webs of material and possible further elements and form a layered composite web;
    at least one cutting device for cutting said layered composite web and forming layered composite articles;
    wherein the plant also comprises a device in accordance with claim 1;
    wherein the web material folded by said device is one of the webs of material and/or the layered composite web.

* * * * *